US008329693B2

(12) United States Patent
Haikala et al.

(10) Patent No.: US 8,329,693 B2
(45) Date of Patent: *Dec. 11, 2012

(54) METHOD FOR THE PREVENTION OF THROMBOEMBOLIC DISORDERS

(75) Inventors: Heimo Haikala, Espoo (FI); Jouko Levijoki, Helsinki (FI); Piero Pollesello, Grankulla (FI); Carola Tilgmann, Jorvas (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/207,537

(22) Filed: Aug. 11, 2011

(65) Prior Publication Data

US 2011/0301166 A1    Dec. 8, 2011

Related U.S. Application Data

(63) Continuation of application No. 11/596,064, filed as application No. PCT/FI2005/000220 on May 12, 2005, now Pat. No. 8,017,609.

(30) Foreign Application Priority Data

May 12, 2004  (FI) ..................................... 20040674

(51) Int. Cl.
*A61K 31/50* (2006.01)
(52) U.S. Cl. ...................................................... 514/247
(58) Field of Classification Search .................. 514/247
See application file for complete search history.

(56) References Cited

U.S. PATENT DOCUMENTS

| 5,512,572 | A | 4/1996 | Haikala et al. |
| 5,945,432 | A | 8/1999 | Bednar et al. |
| 6,303,635 | B1 | 10/2001 | Kawai et al. |
| 6,399,610 | B1 | 6/2002 | Kurkela et al. |
| 6,949,548 | B2 | 9/2005 | Poder et al. |
| 7,485,642 | B2 | 2/2009 | Oldner et al. |
| 8,017,609 | B2 * | 9/2011 | Haikala et al. ............. 514/247 |
| 2006/0166994 | A1 | 7/2006 | Kivikko et al. |
| 2006/0293395 | A1 | 12/2006 | Weil et al. |
| 2007/0032557 | A1 | 2/2007 | Kivikko et al. |

FOREIGN PATENT DOCUMENTS

| EP | 0 565 546 | 3/1995 |
| GB | 1 468 111 | 3/1977 |
| WO | WO 99 66932 | 12/1999 |
| WO | WO 03 004035 | 1/2003 |
| WO | WO 03 063870 A1 | 8/2003 |
| WO | WO 2005 092343 A1 | 10/2005 |
| WO | WO 2007 054514 A2 | 5/2007 |

OTHER PUBLICATIONS

Antila, Saila et al., "Pharmacokinetic and pharmacodynamic interactions between the novel calcium sensitiser levosimendan and warfarin," Eur J Clin Pharmacol, (2000) vol. 56, pp. 705-710.
Chavakis, T., et al., "A Novel Antithrombotic Role for High Molecular Weight Kininogen as Inhibitor of Plasminogen Activator Inhibitor-1 Function;" *Journal of Biological Chemistry* (2002) 227(36):32677-32682.
English language Derwent Abstract of DE 10215240.
Lilleberg, J., et al.; "Dose-Range Study of a New Calcium Sensitizer, Levosimendan, in Patients with Left Ventricular Dysfunction;" *Journal of Cardiovascular Pharmacology* (1995) 26 (Suppl. 1):S63-S69.
Office Action dated Dec. 2, 2010, from copending U.S. Appl. No. 11/596,064.
Office Action dated Apr. 14, 2010, from copending U.S. Appl. No. 11/596,064.
Office Action dated Nov. 25, 2009, from copending U.S. Appl. No. 11/596,064.
Pagel, Paul S. et al., "Influence of levosimendan, pimobendan, and milrinone on the regional distribution of cardiac output in anaesthetized dogs," British Journal of Pharmacology, (1996) vol. 119, pp. 609-615.
Qu, P. et al.; "Time-Course Changes in Left Ventricular Geometry and Function during the Development of Hypertension in Dahl Salt-Sensitive Rats;" *Hypertens Res.* (2000) 23(6):613-623.
Sandell, E.-P., et al.; "Pharmacokinetics of Levosimendan in Healthy Volunteers and Patients with Congestive Heart Failure;" *Journal of Cardiovascular Pharmacology* (1995) 26(Suppl. 1):S57-S62.
Sundberg, Stig et al., "Hemodynamic and Neurohumoral Effects of Levosimendan, a New Calcium Sensitizer, at Rest and During Exercise in Healthy Men," American Journal of Cardiology, (1995) vol. 75, pp. 1061-1066.

\* cited by examiner

*Primary Examiner* — Raymond Henley, III
(74) *Attorney, Agent, or Firm* — Finnegan, Henderson, Farabow, Garrett & Dunner, LLP

(57) ABSTRACT

A method for the prevention of thrombotic, embolic and/or hemorrhagic disorders, such as cerebral infarction (stroke) or myocardial infarction, by administering levosimendan or its metabolite (II) or any of their pharmaceutically acceptable salts to a mammal in need of such prevention.

4 Claims, 1 Drawing Sheet

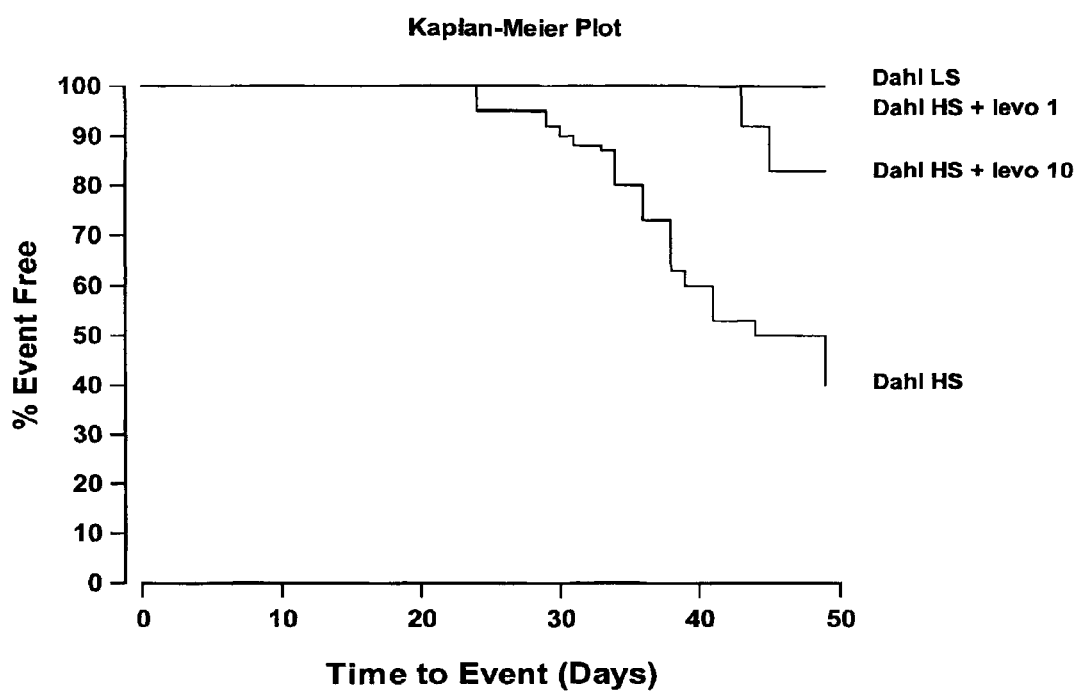

METHOD FOR THE PREVENTION OF THROMBOEMBOLIC DISORDERS

This is a continuation of application Ser. No. 11/596,064, filed Oct. 11, 2007, which issued as U.S. Pat. No. 8,017,609 on Sep. 13, 2011, and which was a national stage application under §371 of PCT International Application No. PCT/FI2005/000220, filed on May 12, 2005, which claims the benefit of priority to Finnish patent application no. 20040674, filed on May 12, 2004.

TECHNICAL FIELD

The present invention relates to a method for the prevention of thrombotic, embolic and/or hemorrhagic disorders, such as cerebral infarction (stroke) or myocardial infarction, by administering levosimendan or its metabolite (II) or any of their pharmaceutically acceptable salts to a mammal in need of such prevention.

BACKGROUND OF THE INVENTION

Thromboembolic disease, i.e. blockage of a blood vessel by a blood clot, affects many adults and can be a cause of death. Most spontaneously developing vascular occlusions are due to the formation of intravascular blood clots known as thrombi, which finally block the artery at the point of their formation. Such occlusions are known as thrombotic occlusions. Alternatively, small fragments of a clot (emboli) may detach from the body of the clot and travel through the circulatory system to lodge in distant organs. These emboli are then trapped and may cause serious complications interfering with normal circulation. Such occlusions caused by a clot that forms elsewhere in the body and travels through the bloodstream are known as embolic occlusions. Cerebral infarction (stroke), myocardial infarction (heart attack) and renal and pulmonary infarcts are well known consequences of thromboembolic phenomena. Obstruction of the blood vessel may also cause a secondary rupture or leakage in arterial walls and subsequent bleeding (haemorrhage). Primary rupture of a blood vessel occurs without thrombotic or embolic occlusion e.g. at the site of aneurysm (weakened area in the wall of artery). Examples of primary cerebral bleeding include intracranial haemorrhage and subarachnoidal haemorrhage.

Fibrin is a major protein component of a clot which forms a relatively insoluble network. Clots are formed when soluble fibrinogen, which is present in high concentrations in blood, is converted to insoluble fibrin by the action of thrombin. Proteolytic, particularly fibrinolytic enzymes, have been used to dissolve vascular occlusions, since disruption of the fibrin matrix results in dissolution of the clot.

Also mammalian blood contains a fibrinolytic system, called plasminogen system, which plays role in thrombolysis. The fibrinolytic system contains plasminogen, which by the action of plasminogen activators (PA) is converted to the active enzyme plasmin, which in turn digests fibrin to soluble degradation products. Two physiological plasminogen activators, called tissue-type (t-PA) and urokinase-type (u-PA), have been identified.

Inhibition of plasminogen activation is achieved by plasminogen activator inhibitor-1 (PAI-1), which forms a stable inactive complex with t-PA. The majority of clot-responsive PAI-1 accumulates within the thrombus rendering it initially resistant to fibrinolysis. An elevated PAI-1 level constitutes an important thrombotic risk factor e.g. for myocardial infarction or deep venous thrombosis because of an overall increased antifibrinolytic potential.

PAI-1 becomes functionally stabilized only in complex with vitronectin (VN), an abundant plasma glycoprotein. Moreover, VN plays a critical role in PAI-1 binding to fibrin. Similar to PAI-1, high molecular weight kininogen (HK) also binds to VN and compete with PAI-1 for proximal binding sites of VN. Thus, kininogen (HK) can inhibit the formation of or dissociate PAI-1-VN complex and thereby contribute to a diminution of PAI-activity. Indeed, studies have shown kininogen (HK) to be antithrombotic rather than prothrombotic, and patients deficient of kininogen (HK) are at increased risk of thrombosis. See Chavakis, T. et al., "A Novel Antithrombotic Role for High Molecular Weight Kininogen as Inhibitor of Plasminogen Activator Inhibitor-1 Function", Journal of Biological Chemistry, 277, 36, 32677-32682 (2002).

An agent capable of preventing thrombotic, embolic and/or hemorrhagic disorders would be highly beneficial in patients who have high risk of thrombotic, embolic and/or hemorrhagic disorders.

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure. Levosimendan increases contractility of the heart by increasing calcium sensitivity of contractile proteins in the cardiac muscle. Levosimendan is represented by the formula:

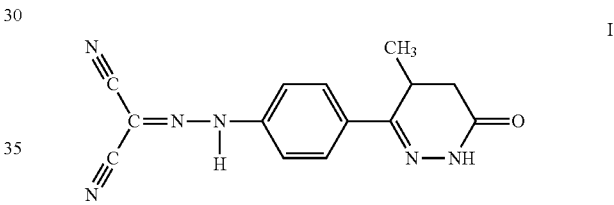

The hemodynamic effects of levosimendan in man are described in Sundberg, S. et al., Am. J. Cardiol., 1995; 75: 1061-1066 and in Lilleberg, J. et al., J. Cardiovasc. Pharmacol., 26(Suppl.1), S63-S69, 1995. Pharmacokinetics of levosimendan in man after i.v. and oral dosing is described in Sandell, E.-P. et al., J. Cardiovasc. Pharmacol., 26(Suppl.1), S57-S62, 1995. Clinical studies have confirmed the beneficial effects of levosimendan in heart failure patients.

Recently it has been found that levosimendan has an active metabolite (R)—N-[4-(1,4,5,6-tetrahydro-4-methyl-6-oxo-3-pyridazinyl)phenyl]acetamide (II) which is present in man following administration of levosimendan. The effects of (II) are similar to levosimendan. The use of (U) for increasing calcium sensitivity of contractile proteins in the cardiac muscle has been described in WO 99/66932.

Administration of levosimendan together with a thrombolytic agent in the treatment of acute myocardial infarction has been described in WO 03/063870. However, it has not been described that levosimendan would have antithrombotic effect or that levosimendan would reduce the risk of thrombotic, embolic and/or hemorrhagic disorders.

SUMMARY OF THE INVENTION

It has now been found that levosimendan and its active metabolite (II) markedly reduce the incidence and volume of brain lesions, behavioural disorders and mortality associated with stroke in salt sensitive rat model. Moreover, levosimendan was found to increase kininogen concentration in rat tissue by ten-fold. The results indicate that levosimendan and its metabolite (II) are able to reduce the risk of thrombotic, embolic and/or hemorrhagic disorders in mammals, such as cerebral infarction (stroke), possibly by kininogen mediated effects. Therefore, levosimendan and its metabolite (II) are useful in the prevention of thrombotic, embolic and/or hemorrhagic disorders and, particularly, in reducing the risk of thrombotic, embolic and/or hemorrhagic events in a mammal, including man, having high risk of such events.

Thus, the present invention provides a method for the prevention of thrombotic, embolic and/or hemorrhagic disorders in a mammal, said method comprising administering to a mammal in need of such prevention an effective amount of levosimendan or its metabolite (II) or any of their pharmaceutically acceptable salts.

The present invention also provides a method of reducing the risk of thrombotic, embolic and/or hemorrhagic event in a mammal having high risk of such events, said method comprising administering to a mammal in need thereof an effective amount of levosimendan or its metabolite (II) or any of their pharmaceutically acceptable salts.

The present invention also provides a method of reducing the risk of thrombotic or embolic occlusion of a blood vessel in a mammal having high risk of such occlusion, said method comprising administering to a mammal in need thereof an effective amount of levosimendan or its metabolite (II) or any of their pharmaceutically acceptable salts.

The present invention also provides the use of levosimendan or its metabolite (II) or any of their pharmaceutically acceptable salts in the manufacture of a medicament for the prevention of thrombotic, embolic and/or hemorrhagic disorders.

The present invention also provides the use of levosimendan or its metabolite (II) or any of their pharmaceutically acceptable salts in the manufacture of a medicament for reducing the risk of thrombotic, embolic and/or hemorrhagic event in a mammal having high risk of such events.

The present invention also provides the use of levosimendan or its metabolite (II) or any of their pharmaceutically acceptable salts in the manufacture of a medicament for reducing the risk of hemorrhage or thrombotic or embolic occlusion of a blood vessel in a mammal having high risk of such hemorrhage or occlusion.

The present invention also provides the use of levosimendan or its metabolite (II) or any of their pharmaceutically acceptable salts in the manufacture of a medicament for preventing hemorrhage or the formation of thrombus or embolus.

Finally, the present invention also provides the use of levosimendan or its metabolite (II) or any of their pharmaceutically acceptable salts in the manufacture of a medicament for preventing stroke.

BRIEF DESCRIPTION OF THE DRAWINGS

FIG. 1 shows the survival (%) of Dahl salt-sensitive rats on high salt diet treated with levosimendan at two different doses (Dahl HS+levo 1 and Dahl HS+levo 10) compared to those for untreated Dahl salt-sensitive rats on high salt (Dahl HS) diet and Dahl salt-sensitive rats on low salt (Dahl LS) diet.

DETAILED DESCRIPTION OF THE INVENTION

As used herein the term "prevention of thrombotic, embolic and/or hemorrhagic disorders" means reducing the incidence or the recurrence of thrombotic, embolic and/or hemorrhagic disorders. Similarly, the term "prevention of stroke" means reducing the incidence or the recurrence of stroke.

As used herein the term "thrombotic and/or embolic disorders" means acute or chronic pathological states or conditions resulting from occlusion or partial occlusion of a blood vessel due to thrombus or embolus. Similarly, the term "thrombotic or embolic occlusion" means occlusion or partial occlusion of a blood vessel due to thrombus or embolus. Examples of thrombotic and embolic disorders include, but are not limited to cerebral thrombotic and embolic disorders such as cerebral infarct (stroke), transient ischemic attack and vascular dementia; thrombotic and embolic disorders of the heart such as myocardial infarct, acute coronary syndrome, unstable angina and ischemic sudden death; pulmonary or renal infarcts, peripheral circulatory disorders and deep vein thrombosis.

As used herein the term "hemorrhagic disorders" means acute or chronic pathological states or conditions resulting from bleeding from damaged blood vessel. Examples of hemorrhagic disorders include, but are not limited to, cerebral hemorrhages such as intracerebral hemorrhage (ICH), subarachnoid hemorrhage (SAH) and hemorrhagic stroke.

One preferred embodiment of the invention is a method for the prevention of cerebral thrombotic, embolic and/or hemorrhagic disorders, in particular cerebral infarct (stroke), transient ischemic attack (TIA), intracerebral hemorrhage (ICH), subarachnoid hemorrhage (SAH) or vascular dementia.

According to another embodiment of the invention, levosimendan or its metabolite (II) or any of their pharmaceutically acceptable salts is used for the prevention of thrombotic, embolic and/or hemorrhagic disorders of the heart, in particular myocardial infarct, acute coronary syndrome and unstable angina.

According to another embodiment of the invention, levosimendan or its metabolite (II) or any of their pharmaceutically acceptable salts is used in the prevention of thrombotic, embolic and/or hemorrhagic disorders independent of inhibiting atrial fibrillation or other cardiac arrhythmias. Patients to be treated may or, according to another embodiment of the invention, may not suffer from atrial fibrillation or other cardiac arrhythmias.

According to another embodiment of the invention, levosimendan or its metabolite (II) or any of their pharmaceutically acceptable salts is used in the prevention of thrombotic, embolic and/or hemorrhagic disorders independent of lowering elevated blood pressure. Patients to be treated may or, according to another embodiment of the invention, may not suffer from hypertension.

According to another embodiment of the invention, levosimendan or its metabolite (II) or any of their pharmaceutically acceptable salts is used in the prevention of thrombotic, embolic and/or hemorrhagic disorders independent of inhibiting myocardial ischemia. Patients to be treated may or, according to another embodiment of the invention, may not suffer from myocardial ischemia.

Conditions which are associated with high risk of thrombotic, embolic and/or hemorrhagic disorders include, but are not limited to, earlier thrombotic, embolic and/or hemorrhagic event; orthopedic fractures or other injuries; prolonged bed rest; chronic deep venous insufficiency of the legs; diabetes; elevated blood lipid levels; atherosclerosis; endocarditis; carcinoma; pregnancy; and postoperative periods of surgical operations such as cardiac interventions, percutaneous coronary intervention, angioplasty and prosthetic valves.

The method according to the invention relates to administering to a subject an amount of levosimendan or its metabolite (II) or any of their pharmaceutically acceptable salts which is effective to prevent thrombotic, embolic and/or hemorrhagic disorders, preferably by inhibiting blood clot formation and/or by inducing fibrinolysis of blood clot. Without wishing to be bound to a theory, it is contemplated that levosimendan, at least partly, prevents thrombotic, embolic and/or hemorrhagic disorders by increasing kininogen expression and/or secretion. Preferably, levosimendan prevents thrombotic, embolic and/or hemorrhagic disorders without affecting the hemostatic balance, that is, without significantly inhibiting platelet aggregation or blood coagulation.

The administration of levosimendan or its active metabolite (II) can be enteral, e.g. oral or rectal; parenteral, e.g. intravenous; or transdermal or transmucosal.

The effective amount of levosimendan or its active metabolite (II) to be administered to a subject depends upon the condition to be treated or prevented, the route of administration, age, weight and the condition of the patient. Oral daily dose of levosimendan or its active metabolite (II) in man ranges generally from about 0.05 to about 10 mg. For the long-term prevention of thrombotic, embolic and/or hemorrhagic disorders in man, relatively low oral doses are generally preferred, e.g. an oral daily dose from about 0.05 to about 5 mg, preferably from about 0.1 to about 4 mg, more preferably from about 0.2 to about 3 mg.

Levosimendan can be administered by intravenous infusion using the infusion rate from about 0.01 to about 5 μg/kg/min, more typically from about 0.02 to about 3 μg/kg/min. The active metabolite (II) can be administered intravenously using an infusion rate, which is from about 0.001 to about 1 μg/kg/min, preferably from about 0.005 to about 0.5 μg/kg/min.

The active ingredient of the invention may be administered daily or several times a day or periodically, e.g. weekly or biweekly, depending on the patient's needs.

For the prevention of thrombotic, embolic and/or hemorrhagic disorders, oral administration is particularly preferred. Particularly preferred active ingredient is levosimendan or a pharmaceutically acceptable salt thereof.

Levosimendan or its active metabolite (II) is formulated into dosage forms suitable for the prevention of thrombotic, embolic and/or hemorrhagic disorders using the principles known in the art. It is given to a patient as such or preferably in combination with suitable pharmaceutical excipients in the form of tablets, granules, capsules, suppositories, emulsions, suspensions or solutions whereby the contents of the active compound in the formulation is from about 0.1 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

According to one embodiment of the invention the dosage form contains levosimendan or its active metabolite (II) as a sole active agent, preferably with package instructions to use the medicament in preventing thrombotic, embolic and/or hemorrhagic disorders, particularly in preventing hemorrhage or thrombotic or embolic occlusion of a blood vessel.

According to another embodiment of the invention the dosage form contains levosimendan or its active metabolite (II) together with any other active ingredient useful in preventing thrombotic, embolic and/or hemorrhagic disorders.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.05 to 10 mg, more typically from about 0.2 to 4 mg, of levosimendan or its active metabolite (II).

Formulations suitable for intravenous administration such as injection or infusion formulation, comprise sterile isotonic solutions of levosimendan or its active metabolite (II) and vehicle, preferably aqueous solutions. Typically an intravenous infusion solution comprises from about 0.01 to 0.1 mg/ml of levosimendan or its active metabolite (II).

Salts of levosimendan or its active metabolite (II) may be prepared by known methods. Pharmaceutically acceptable salts are useful as active medicaments, however, preferred salts are the salts with alkali or alkaline earth metals.

PHARMACEUTICAL EXAMPLES

Example 1

Oral Capsule

Hard gelatin capsule size 3
Levosimendan 2.0 mg
Lactose 198 mg

The pharmaceutical preparation in the form of a capsule was prepared by mixing levosimendan with lactose and placing the powdery mixture in hard gelatin capsule.

Example 2

Concentrate Solution for Intravenous Infusion (a) levosimendan 2.5 mg/ml
(b) Kollidon PF12 10 mg/ml
(c) citric acid 2 mg/ml
(d) dehydrated ethanol ad 1 ml (785 mg)

The concentrate solution was prepared by dissolving citric acid, Kollidon PF121 and levosimendan to dehydrated ethanol in the sterilized preparation vessel under stirring. The resulting bulk solution was filtered through a sterile filter (0.22 μm). The sterile filtered bulk solution was then aseptically filled into 8 ml and 10 ml injection vials (with 5 ml and 10 ml filling volumes) and closed with rubber closures.

The concentrate solution for intravenous infusion is diluted with an aqueous vehicle before use. Typically the concentrate solution is diluted with aqueous isotonic vehicles, such as 5% glucose solution or 0.9% NaCl solution so as to obtain an aqueous intravenous solution, wherein the amount of levosimendan is generally within the range of about 0.001-1.0 mg/ml, preferably about 0.01-0.1 mg/ml.

EXPERIMENTS

Experiment 1

Effects on Mortality in Salt Sensitive Rat Model

Effect of levosimendan on early stage mortality of Dahl salt-sensitive rats was studied. Dahl salt-sensitive rats on high salt diet develop hypertension and increased mortality. In the early stages of hypertension the incidence of death is almost entirely due to stroke and sudden death. See Qu, P. et al., Hypertens. Res., 2000; 23:613-623.

6-week-old male Dahl salt-sensitive rats (SS/JrHsd) received the following diet and drug regimens for 7 weeks: 1) Dahl SS controls on high salt diet, 2) Dahl SS rats on high salt diet+high-dose levosimendan (10 mg/l of levosimendan in drinking water), 3) Dahl SS rats on high salt diet+low-dose levosimendan (1 mg/l of levosimendan in drinking water) and 4) Dahl SS controls on low salt diet. High salt diet was produced by adding NaCl to commercial low salt diet.

The early survival results are shown in FIG. 1 as Kaplan-Meier Plot. Only 38% (9/24) of rats on high salt diet survived the 7-week follow up period. None of the rats in the low-dose levosimendan group (n=12) died, and only three out of 12 rats died in the high dose levosimendan group. Thus, levosimedan markedly reduced the early stage mortality of salt-sensitive rats suggesting beneficial effect of levosimendan on stroke-related mortality.

Experiment 2

Effects on the Incidence of Strokes in Salt Sensitive Rat Model

Effect of levosimendan on the incidence of cerebral strokes in Dahl salt-sensitive rat stroke model was studied using Magnetic Resonance Imaging (MRI) and behavioural tests (Neuroscore and Functional Observational Battery (FOB)).

Dahl SS rats were divided into three treatment groups: High-Salt diet+vehicle (n=20), High-Salt diet+Levosimendan 1 mg/kg/day (n=20), and Normal-Salt diet control (n=4). High salt diet contained 7% of NaCl in commercial low salt diet. Feeding with the high-salt diet was started at the age of 6 weeks and continued 7 weeks until the end of the study. Levosimendan was administered via drinking water (2 mg/l of levosimendan in drinking water). The administration was started at the same time as the high-salt diet and continued until the end of the study. The consumption of drinking water and food as well as the body weight and general health of the animals were monitored. MRI was performed once-a-week during the weeks 2-8. FOB and 7-point Neuroscore testing were performed once-a-week during the weeks 1-3 and twice-a-week during weeks the 4-8.

Mortality:

All animals fed with control diet survived until the end of the study. Only one animal (5%) in the levosimendan group died during the study, whereas in the vehicle group mortality reached 70% at the end of the study.

In Vivo MRI:

Diffusion and T2-weighted MRI using Varian Inova console interfaced to a 4.7 T horizontal magnet (Magnex Scientific Ltd.) was performed once-a-week on halothane-anesthetized rats. T2-weighted imaging and quantitative diffusion imaging were used to determine lesion size and to characterize plausible ischaemic lesions in Dahl SS rats. Typical lesions were heterogeneous and consisted of several different regions with different MRI characteristics. Hyperintensity in T2-weighted imaging was found in practically all animals with detectable abnormalities. This can be interpreted as oedematous tissue, which is typical for ischaemic tissue and is, in general, detectable starting at ~12-24 h after occlusion of the feeding vessel. Furthermore, most of the ischemic animals showed local signal void areas within the hyperintense lesion area. At the high magnetic field (4.7 T) used in this study, any ferromagnetic substance causes local disruption in magnetic field homogeneity which destroys the signal in T2-weighted imaging. This is a characteristic MRI feature for hemorrhage as haemoglobin in blood contains Fe. Thus almost all lesions detected in this study can be characterized to be associated with hemorrhage.

Vehicle treated animals had higher incidence of strokes and larger stroke volumes compared to levosimendan treated group. On the 6$^{th}$ week of the study, more than 50% of the vehicle treated animals had noticeable T2-weighted MRI changes whereas no changes were observed in levosimendan treatment group at that time. At the last MRI measurement, detectable T2-weighted MRI changes were observed in 10% of levosimendan treated animals and in 85% of vehicle treated animals (Table 1). Abbreviations: LS, levosimendan.

TABLE 1

| | | T2-lesion volumes (mm$^3$) | | | | | | |
|---|---|---|---|---|---|---|---|---|
| | Week | 2 | 3 | 4 | 5 | 6 | 7 | 8 |
| Control | 0 | 100% | 100% | 100% | 100% | 100% | 100% | 100% |
| | n | 4 | 4 | 4 | 4 | 4 | 4 | 4 |
| LS | 0 | 95% | 100% | 95% | 100% | 100% | 90% | 89% |
| | 1-50 | 5% | 0% | 5% | 0% | 0% | 0% | 5% |
| | 51-100 | 0% | 0% | 0% | 0% | 0% | 10% | 0% |
| | >200 | 0% | 0% | 0% | 0% | 0% | 0% | 5% |
| | n | 20 | 20 | 20 | 20 | 20 | 20 | 19 |
| Vehicle | 0 | 100% | 100% | 100% | 100% | 53% | 33% | 14% |
| | 1-50 | 0% | 0% | 0% | 0% | 20% | 17% | 14% |
| | 51-100 | 0% | 0% | 0% | 0% | 7% | 25% | 14% |
| | 101-200 | 0% | 0% | 0% | 0% | 13% | 8% | 0% |
| | >200 | 0% | 0% | 0% | 0% | 7% | 17% | 57% |
| | n | 20 | 20 | 19 | 17 | 15 | 12 | 7 |

Ex Vivo MRI:

For ex-vivo imaging post-mortem brain was removed from the skull and immersed into 4% formalin for 48 h and thereafter stored in 0.1 M PBS. The brain was embedded in perfluoropolyether and MRI was performed in 9.4 T magnet (Oxford) interfaced to a SMIS-console. The interpretation of hyperintensity and signal void areas follows that presented for in vivo studies. In ex vivo studies only mature lesions with significant oedema and destructed tissue structure can be detected. Initial T2 contrast, which may be detectable in vivo, may not be visible in ex vivo studies. The findings in ex vivo studies support the idea that most of the ischemic lesions were associated with hemorrhage. Ex vivo MRI also revealed that vehicle treated animals had higher incidence of strokes and larger stroke volumes compared to levosimendan treated group (Table 2). Abbreviations: LS, levosimendan.

TABLE 2

Incidence of T2 changes

| Control | 0 | 100% |
|---|---|---|
|  | n | 4 |
| LS | 0 | 80% |
|  | 1-50 | 20% |
|  | 51-100 | 0% |
|  | >200 | 0% |
|  | n | 20 |
| Vehicle | 0 | 10% |
|  | 1-50 | 60% |
|  | 51-100 | 20% |
|  | 101-200 | 10% |
|  | >200 | 0% |
|  | n | 20 |

Behavioural Testing:

Functional observational battery (FOB) and Neuroscore testing were performed once-a-week during weeks 1-3 and twice-a-week during weeks 4-8.

a) Neuroscore:

A seven-point neuroscore test was used to assess motor and behavioral deficits (modified from Zausinger et al. Brain Res. 863:94-105, 2000). The neurological test was conducted by an investigator blinded to the treatment status of the rats. The seven-point scale was as follows:

Grade 6: Normal extension of both forelimbs towards the floor when lifted gently by the tail.

Grade 5: Consistent flexion of either of the forelimbs, varying from mild wrist flexion and shoulder adduction to severe posturing with full flexion of wrist, elbow, and adduction with internal rotation of the shoulder, when lifted gently by the tail.

Grade 4: Consistently reduced resistance to lateral push towards either side.

Grade 3: Circling towards either side if pulled and lifted by the tail.

Grade 2: Circling towards either side if pulled by the tail.

Grade 1: Spontaneous circling towards either side.

Grade 0: No spontaneous movements.

Results:

Control animals as well as the animals fed with levosimendan scored maximum scores throughout the study, whereas the scores in vehicle group started to decrease starting from the 5$^{th}$ week of the study.

b) FOB:

All rats were observed using standardized procedures. The procedures included observation of rats in the home cage, while moving in open arena and through manipulative tests. The measures included:

(1) Home-Cage Measurements:

Body position, Respiration, Vocalization and Palpebral closure.

(2) Hand-Held Observations:

Reactivity when picked up, Handling, Lacrimation, Salivation, Piloerection and Others (hair cast, bite marks, missing nails, gauntness, etc.).

(3) New Environment/Open Field Activity:

Number of rearings I (rat does not use forelimbs), Number of rearings II (rat supports itself on wall), Clonic involuntary movement, Tonic involuntary movement, Gait, Activity, Arousal, Occurrence of stereotypic movements, Abnormal behavior, Number of defecations and Number of urinations.

(4) Stimulus Response:

Approach response, Touch response, Eyelid reflex, Pinna reflex, Sound response and Tail pinch response.

(5) Nervous and Muscle Measurements:

Abdominal tone, Limb tone and Grip strength.

(6) Rectal Body Temperature:

(7) Additional Data:

Eye color, Air way mucus secretion and Peripheral blood circulation (auricles, toes, tail, nose).

Results:

Levosimendan was found to markedly reduce and postpone stroke-associated behavioural deficits observed in FOB testing.

In summary, the experiment shows that levosimendan reduces and/or postpones mortality, incidence and volume of brain lesions, and behavioural disorders associated with cerebral strokes in Dahl SS rats when the treatment is started preventatively.

Experiment 3

Effect on Kininogen Expression

Method

Rats were given levosimendan orally 20 mg/l in tab water and controls only tab water for eight days. Hearts were frozen in liquid nitrogen and stored at −80° C. The heart tissues were lyophilized on ice over night and incubated in lysis buffer; 9 M urea, 20 mM Tris-HCl pH 7.4, 50 mM KCl, 3 mM EDTA pH 7.5, 0.5% IPG buffer 3-10 NL, 5 mM PMSF, 1% DTT and Benzoase 100 Units for 10 min at room temperature. The protein solution was then sonicated 2×15 s and centrifuged at 14000 rpm for 5 min. The supernatants were collected and the protein amount measured based on the protein assay kit from BioRad. 40 µg protein solution was diluted in 350 µl of rehydration buffer; 7 M urea, 2 M thiourea, 2 mM TBP, 0.5% IPG buffer 3-10 NL, 4% CHAPS and 0.2% BFB, incubated for 30 min at room temperature and centrifuged for 5 min at 14000 rpm.

350 µl of supernatant was applied on an IPG strip 18 cm, pH 3-10 NL (Amersham Pharmacia Biotech) and the strips were put in strip holders. 600 µl of paraffinoil was applied on top of each strip and the strips were then run on an IPGphor electrophoresis unit according to the following program:

0 V 7 h,
20 V 7 h,
100 V 5 h,
500 V 1 h,
1000 V 1 h,
3000 V 1 h,
8000 V 5.5 h

The focused strips were equilibrated in the following buffer: 6 M urea, 50 mM Tris-HCl, pH 8.8, 2% SDS, 30% glycerol, 2% DTT, 2.5% iodoacetamide and 0.2% BFB 2×10 min at room temperature. The strips were then applied on an 11% SDS-PAGE and covered by 0.75% agarose and run at 4° C. 100 V for 4 h. SDS-PAGE gels were stained by silver staining according to the commercially available kit (PlusOne) from Amersham Pharmacia Biotech. After staining the gels were scanned with imaging densitometer (Calibrated imaging densitometer GS-710, Biorad). The silver stained gels were analyzed by PD-QUEST(6.2) 2-DE software (BIO-RAD). After the protein spot detection and gel editing, a match set was constructed from 6 gels: three replicates of levosimendan hearts and three of controls. The gel analysis was done by comparing the levosimendan sample against the control. The twofold difference in O.D. was used as a threshold value for differential protein expression.

Based on PD-QUEST analysis the stained protein spots were cut from the gel and the silver stained gel slices were stored at −20° C. The protein digestion for mass fingerprinting was done according to the in-gel digestion procedure (Rosefeld, J. et al., Anal. Biochem., 203:173-179, 1992). Before the digestion, the protein was reduced and alkylated. The proteins were digested by 2 µl of modified trypsin solution at a concentration of 0.04 µg/µl (Sequencing Grade Modified Trypsin, porcine, Promega).

All samples were prepared by reversed phase pipette tips $C_{18}$ (ZipTip, Millipore). The sample 3 µl was eluted in a-cyano-4-hydroxycinnamic acid diluted in 50% acetonitril and 0.1% trifluoroacetic acid and the sample applied onto the MALDI-TOF sample plate. The samples were analyzed in a TOF mass spectrometer (Voyager-DE PRO). The mass analysis was completed by positive ionization mode, and the mass range for time-of-flight parent mass computation covered MHz of 500-3500. The masses of the obtained peptides were analysed by the MS-fit program on the Expasy Molecular Biology server PeptIdent.

Results

The extracts of rat hearts levosimendan/control were analyzed on 2-DE gels and based on silver staining analysis we obtained totally about 1500 spots. A ten fold up-regulated protein expression was seen for a protein that matched the SWISS PROT identification number P08934 Chain 1: Kininogen-Rattus novergicus pI 6.22 with the molecular weight of 68.9 kDa.

The invention claimed is:

1. A method for reducing the risk of a thrombotic, embolic and/or hemorrhagic disorder in a mammal, wherein said mammal does not suffer from myocardial ischemia, said method comprising administering to a mammal who is at risk of a thrombotic, embolic and/or hemorrhagic disorder an effective amount of levosimendan or its metabolite (II):

(R)—N-[4-(1,4,5,6-tetrahydro-4-methyl-6-oxo-3-pyridazinyl)phenyl]acetamide (II) or a pharmaceutically acceptable salt of levosimendan or its metabolite (II).

2. The method according to claim 1, wherein the thrombotic, embolic and/or hemorrhagic disorder is pulmonary or renal infarct, peripheral circulatory disorder or deep vein thrombosis.

3. The method according to claim 1, wherein the thrombotic, embolic and/or hemorrhagic disorder is a myocardial infarct.

4. A method of reducing the risk of a hemorrhage or a thrombotic or embolic occlusion of a blood vessel in a mammal having a high risk of hemorrhage or thrombotic or embolic occlusion of a blood vessel, wherein said mammal does not suffer from myocardial ischemia, said method comprising administering to the mammal an effective amount of levosimendan or its metabolite (II):

(R)—N-[4-(1,4,5,6-tetrahydro-4-methyl-6-oxo-3-pyridazinyl)phenyl]acetamide (II) or a pharmaceutically acceptable salt of levosimendan or its metabolite (II).

* * * * *